United States Patent [19]

Hendricks

[11] E Re. 31,564

[45] Reissued Apr. 24, 1984

[54] HYPEREXTENSION BACK BRACE

[76] Inventor: David A. Hendricks, c/o Cash Manufacturing 2303 E. Washington, Bloomington, Ill. 61701

[21] Appl. No.: 320,835

[22] Filed: Nov. 12, 1981

Related U.S. Patent Documents

Reissue of:

[64] Patent No.: 4,173,973
Issued: Nov. 13, 1979
Appl. No.: 920,937
Filed: Jun. 30, 1978

[51] Int. Cl.[3] ..... A61F 5/02
[52] U.S. Cl. ..... 128/78
[58] Field of Search ..... 128/78, 68, 82, 83

[56] References Cited

U.S. PATENT DOCUMENTS 2,582,930 1/1952 Jewett ..... 128/78
2,808,050 10/1957 Ward ..... 128/78

OTHER PUBLICATIONS

La-Cal Surgical Supplies, Inc. Brochure for Hyperextension Brace Nos. 1004, 1005, prior to Jun. 30, 1977.
Florida Brace Corp. Brochure, J-35, Jewett Hyperextension Orthosis, prior to Jun. 30, 1977.
Pel Supply Co. Brochure, Becker Models L-25, L-26, prior to Jun. 30, 1977.
Pel Supply Co. Brochure Spencer Medical Models SCO35, SCO34, prior to Jun. 30, 1977.
Bremer Brace Mfg. Co. Brochure for Hyperextension Brace, prior to Jun. 30, 1977.

*Primary Examiner*—John D. Yasko
*Attorney, Agent, or Firm*—Hill, Van Santen, Steadman, Chiara & Simpson

[57] ABSTRACT

A hypertension brace of cruciform shape having four pads, including sternal, pubic and two side pads, in which each of the four arms is longitudinally adjustable so as to facilitate fitting the patient. Further, at least the sternum pad is flexibly mounted to enable easy comformability to the sternum area of the individual patient.

18 Claims, 9 Drawing Figures

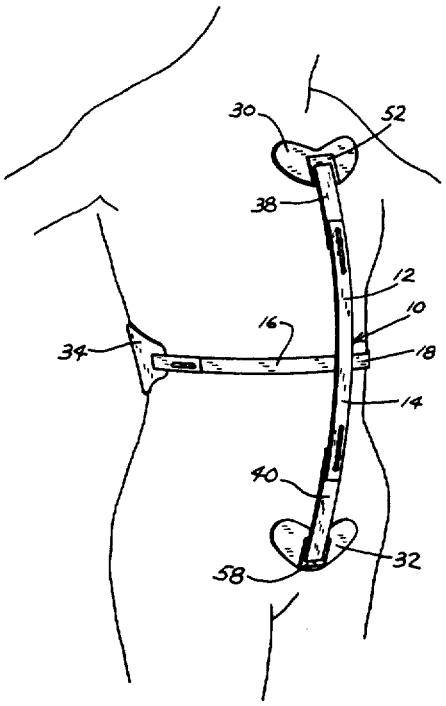
FIG. 1
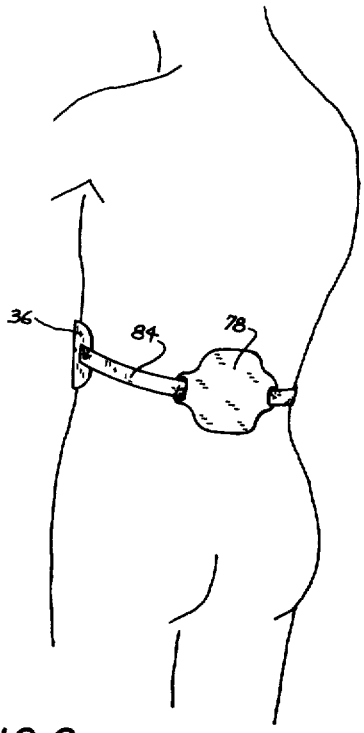
FIG. 2
FIG. 9
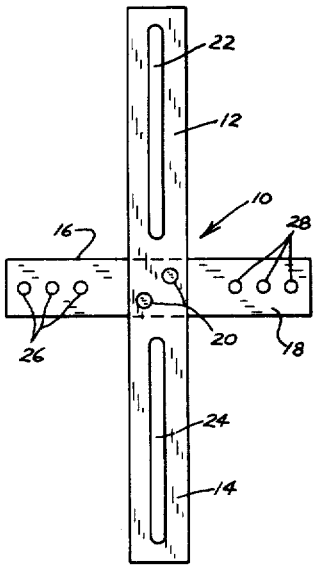

FIG. 5
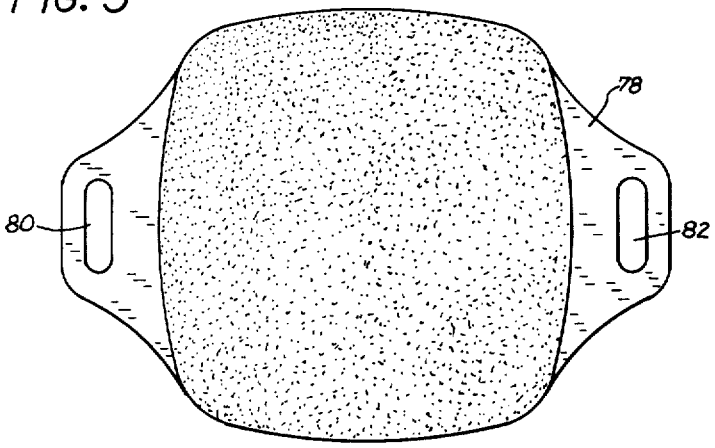
FIG. 8
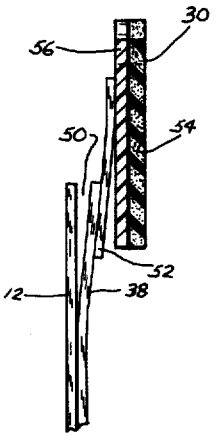
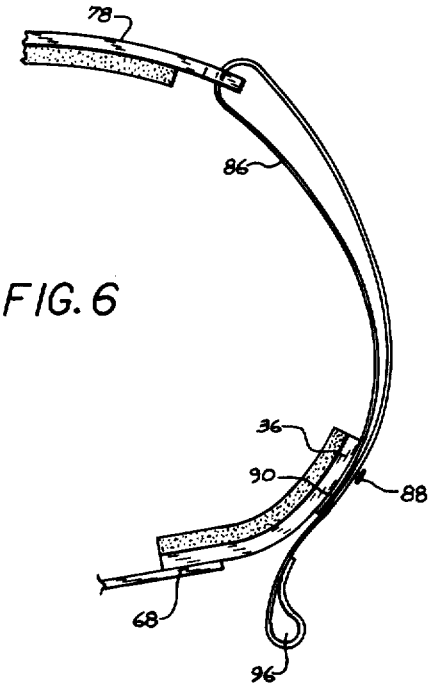
FIG. 6

HYPEREXTENSION BACK BRACE

Matter enclosed in heavy brackets [ ] appears in the original patent but forms no part of this reissue specification; matter printed in italics indicates the additions made by reissue.

*This application is a reissue of Ser. No. 920,937 now U.S. Patent 4,173,973.*

BACKGROUND OF THE INVENTION

Hyperextension braces of various types are well known for the relief of patients suffering from various diseases and deformities of the spinal area, the principal purposes of such braces being to apply forces in relief of pains associated with those departures from normal. Fundamentally, a typical brace is applied from the front or anterior of the thoracic area of the human body, in conjunction with a back pad and straps or the like for tensioning the front and back structures in such manner as to cause hyperextension of the posterior or thoracolumbar. In one well known example (e.g., the Model 8141, manufactured and sold by the Freeman Mfg. Corp. of Sturgis, Mich., circa 1975–76), the front part is a cruciform structure having upper and lower arms and right and left arms, each having an appropriate pad for bearing on four anterior areas of the thoracic part of the human body, together with a back or lumbar pad, the latter being connected adjustably to the side pads by straps or the like, by means of which suitable tensional forces could be applied so as to hyperextend the patient's back.

So far as is known, there seems to have been little patent activity in this specific area; although the U.S. Pat. to Bell, No. 2,181,689 does deal with a spinal brace in which the posterior and anterior portions of the body are compressed.

Considering the Freeman and Bell structures in the most favorable light, much is left to be desired so far as concerns economy of manufacture, ease of application, and adaptability to the patient because of lack or difficulty of adjustment, failure to concentrate on critical areas of the body and lack of conform the pads to variations in the bodies of different patients.

SUMMARY OF THE INVENTION

According to the present invention, numerous significant improvements are made over the known prior art, residing mainly in the provision of longitudinal adjustability of the pad-carrying arm parts. More particularly this is achieved by providing a basic cruciform structure of rigid nature, having four arms, two of which are vertical and the other two of which are horizontal. The free ends of the vertical arms are fitted with sternum and pubic pads respectively and the free ends of the horizontal arms are fitted with right and left side pads engageable with side portions of the body, primarily in the areas of the right and left rib cages. As a basic improvement, each of the arms of the cruciform structure carries a supplementary or movable part and each of these movable parts carries its associated pad. Thus the supplementary arms are selectively and individually adjustable, with their pads, lengthwise of the respective fixed arms, which adjustment is quickly and easily made to accommodate the structure to the patient. Preferably, each movable arm part is interconnected by slot and screw means to its associated fixed part to accomplish the relative longitudinal adjustment.

A further feature resides in the attachment of at least the sternum and pubic pads to their respective movable arm parts by flexible elements that enable flexing of each pad about a plurality of axes, as distinguished from a typical single-axis hinge or pivot, thus rendering the pad more easily conformable to the sternum and pubic areas of the patient. A still further feature in this respect is that the movable arm part of the sternum pad is offset from its fixed arm part in the direction toward the body, still further improving the contact at the sternum area.

The sternum pad differs, for example, from the Freeman pad in that in its shape is somewhat arcuate as seen from the front, so that its top edge is concave and its bottom edge is convex.

The means for securing the back pad to the side pads is improved by the use of a flexible or pliant element, preferably in the form of straps, there being two of these, one attached to each side pad and reeved thru a slot in the back pad and returned to the associated side pad for attachment, the element or strap having therein a plurality of lengthwise spaced-apart apertures receivable over a stud or the like on the side part. The free end of the strap is provided with a finger loop to facilitate manipulation.

Further features and objects inherent in and encompassed by the invention will appear to those skilled in the art as a preferred embodiment of the invention is depicted in detail and described in the ensuing drawings and description.

BRIEF DESCRIPTION OF THE DRAWING

FIG. 1 is an overall perspective view of the invention as applied to the human body, as seen from the right front of the patient, the associated body portion being shown in broken lines.

FIG. 2 is a similar view as seen from the left rear of the patient.

FIG. 5 is a view of the back pad per se.

FIG. 6 is a fragmentary plan showing the connection between one side of the back pad and its associated side pad.

FIG. 8 is a view as seen along the line 8—8 of FIG. 3, showing the offset between the sternum movable and fixed arms.

FIG. 9 is an elevation of the basic cruciform structure, less its adjustable components.

DESCRIPTION OF THE PREFERRED EMBODIMENT

Figure 3:
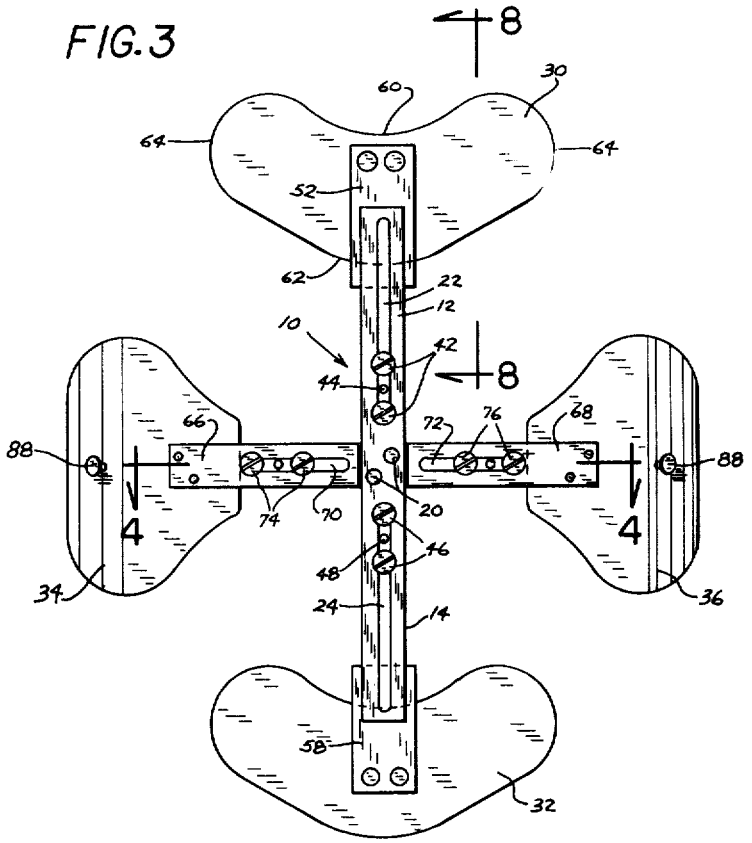
FIG. 3 is a view of the front or anterior part of the structure per se, on a scale larger than that used in FIGS. 1 and 2.
Figure 7:
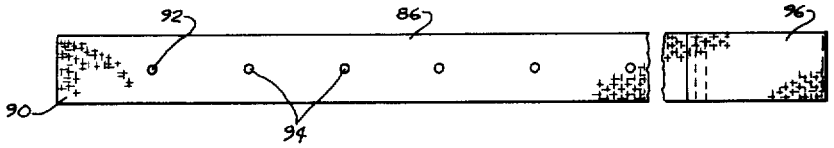
FIG. 7 is an elevation, with a portion broken away of a strap as used between the back pad and a side pad.

The basic part of the brace is the cruciform structure shown at 10 (FIG. 9), having upper and lower vertically alined vertical arms 12 and 14 and right and left horizontally alined horizontal arms 16 and 18. Preferably, these consist of two strips of aluminum or the like, crossed *with the vertical arms attached to the outward side of the horizontal arms as seen in FIGS. 1, 3, 4 and 9* and centrally secured together by rivets, as at 20. The structure is shaped so as to be concave toward the body (FIGS. 1, 2, 4 and 8). The upper arm has a longitudinal slot 22, the lower arm a longitudinal slot 24, and the arms 16 and 18 have pluralities of threaded bores 26 and 28, respectively. As will be seen below, these comprise parts of the means for adjustably mounting movable arms on the fixed arms 12, 14, 16 and 18[.] *to provide a maximum range of sizes from a single device.* The latter arms are considered fixed because they are rigid with each other because of the riveted attachment at 20.

In the known prior art, especially in the Freeman device, arms equivalent to the arms 12, 14, 16 and 18, carry pads for body contact. In the present invention, four pads are used, comprising a sternum pad 30, a pubic pad 32 and right and left side pads 34 and 36. In contradistinction to the prior art, the present invention utilizes supplementary adjustable arms for mounting the pads on the basic structure 10. Thus, the sternum pad 30 is mounted on a movable arm part 38 (FIG. 8), and the pubic pad 32 is mounted on a movable lower arm part 40 (FIG. 1). The upper or sternum arm part 38 is slidably carried by the fixed or basic upper arm part 12 by means of the slot 22 and a set (here a pair) of securing means in the form of screws 42 threaded into two of three threaded bores (one visible at 44 in FIG. 3) in the movable arm part 38. The movable lower arm part 40 carries the pubic pad 32 and is similarly carried on the lower fixed arm part 14 via the slot 24 and a pair of screws 46 threaded into two of three threaded bores 48, one of which is seen in FIG. 3. *The movable upper arm part 38 and lower arm part 40 are positioned on the inner side of the fixed arms 12, 14 as seen in FIGS. 1, 3 and 8.*

The normal ranges of adjustability, the two outer bores 44 (or 48) are used to receive the screws 42 (or 46) to achieve stability, but when a greater range of adjustability is required, the outermost screw may be used in the next adjacent bore, thus increasing the range by, say [1.3] *3.8* cm (1½ in.). *Therefore, one device can be of a universal size capable of being adjusted to all standard adult sizes.*

It will be seen from FIG. 8 that the free end of the movable arm part 38 is slightly offset at 50 inwardly as respects the posterior of the patient, thus improving the sternum-to-sternum pad contact, supplemented by a flexible attachment element 52 secured to the front side of the sternum pad 30, and the rear side of the arm part 38. The sternum pad 30, like the other pads, is preferably constructed of plastic, having a rigid layer [54] *56* and a foamed or resilient [56] *54.* The plastic used may be of any acceptable type, such as polyethylene or polypropylene, bonded together in any suitable manner. The attachment element 52 is likewise plastic, bonded to the pad 30 and arm part 38 and is of such nature as to provide a "living" hinge, i.e., it is permanent even through it is capable of flexing about a plurality of axes so as to partake of bending, twisting, etc. thus enabling the sternum pad to readily conform to variations in sternum shapes and forms. A flexible element 58, like the element 52, similarly connects the pubic pad 32 to the lower movable arm part 40.

It is to be noted that the sternum pad has a shape quite different from pads of the prior art, being of generally arcuate shape as seen from the front, having an upper concave edge 60, a lower convex edge 62 and rounded side edges 64 joining or fairing into the aforesaid edges. These edges are designed to give the wearer greater freedom of movement in the neck area while still applying the necessary contact forces to surrounding parts of the body. *It should also be noted that the pubic pad 32 has a shape identical to that of the sternum pad 30 seen in FIGS. 1 and 3 allowing a single die to punch the two pads thereby lowering manufacturing costs.*

Figure 4:
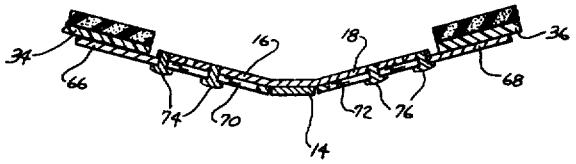
FIG. 4 is a fragmentary sectional view, on an enlarged scale, as seen along the line 4—4 on FIG. 3.

The side pads 34 and 36 are mounted respectively on moveable arm parts 66 and 68 (FIGS. 3 and 4) via the threaded bores 26 and 28 and slots 70 and 72 respectively in the arms, together with sets (here pairs) of screws 74 and 76. *The movable arm parts 66 and 68 are positioned on the outer side of the fixed arms 16, 18 as seen in FIGS. 1, 3, 4 and 9. Thus, the assembly of fixed arms 12, 14, 16 and 18 and movable arms 38, 40, 66 and 68 as seen in FIGS. 3 and 4 is never more than two arms thick.* What has been said about the slot and screw means 22, 42 and 44 and 24, 46 and 48 above, applies here as to slidable adjustability and range of adjustment. *The side pads 34 and 36 are formed in a curved manner as shown in FIG. 6 and are to be positioned at the front of the patient's side as FIGS. 3, 4 and 6 illustrate and not directly at the side as is universally done in the prior art. This frontside positioning permits the slidable adjustability required for universal sizing which is not available in prior art devices.*

Typical of a hyperextension brace is the use of a back pad and means connecting same to the front structure to apply forces to the back or lumbar area. In the present case a back pad 78 is used, here to the same dual-layer construction as those previously described. The back pad has slots 80 and 82 in wing or rear portions at opposite sides thereof (FIG. 5) and these are used in conjunction with means for securing the back pad to the side pads 34 and 36. The preferred securing means comprises right and left pliant elements in the form of straps 84 and 86 (FIGS. 1, 2, 6 and 7). Since these are identical (although symmetrical) in the present case, only the strap 86 needs description in detail. As best seen in FIG. 6, the pad 36 has an outwardly protruding stud or the like 88 to which the inner end 90 of the strap is attached, the strap having a suitable aperture 92 therein. The strap, so attached to the stud 88, which may be headed to prevent accidental dislodgment of the strap, is reeved thru the associated slot 82 in the back pad and returned to the stud 88, to which it may be attached by any one of a plurality of apertures 94 spaced equally apart lengthwise of the strap. A preferred spacing is about 3 cm (1½ in.). Each strap is provided with a finger loop 96 at its free end to facilitate manipulation, the purpose of the adjutability being to secure the proper application of forces between the posterior structure 10 and the back pad 78, depending upon the dimensions, condition etc of the patient.

I claim:

1. A [hypertension] *hyperextension* brace including a rigid main cruciform structure adapted to overlie the anterior thoracic area of the human body and having upper and lower vertically [alined] *aligned* vertical arms and right and left [horizontal alined] *horizontally aligned* horizontal arms, sternum and pubic pads disposed respectively at the free ends of the upper and lower arms and right and left side pads disposed respectively at the free ends of the right and left arms, a back pad for contact with the back of the body and right and left means for attaching the back pad to the right and left pads, characterized in that each arm is of two-piece construction comprising a fixed part forming a rigid part of the cruciform structure and a movable part longitudinally adjustable relative to its fixed part, the pads being affixed respectively to the movable parts, and a plurality of means is provided for securing the movable parts in individually selected positions.

2. The brace defined in claim 1, further characterized in that at least the sternum pad is attached to its respective movable arm part by flexible means enabling the sternum pad to flex about a plurality of axes so as to render it capable of more readily conforming to the sternum area with which it is associated.

3. The brace defined in claim 1, further characterized in that each of the right and left means securing the back pad to the right and left side pads is an elongated pliant element attached to the respective right and left pad, reeved through slot means in the back pad and returned to the respective right or left pad, each element having a finger loop at its free end for facilitating the tensioning of the element, and each element being adjustably attachable to its respective right or left side pad for accommodating different body dimensions.

4. The brace defined in claim 1, further characterized in that the sternum pad is of generally arcuate shape as seen from the front, having a concave upper edge portion, a convex lower edge portion, and side edge portions joining the aforesaid portions.

5. The brace defined in claim 1, further characterized in that the movable arm part for the sternum pad is offset from the free end of its associated fixed arm part in the direction toward the body with which the brace is used.

6. The brace defined in claim 1, further characterized in that each movable arm part is carried on its respective fixed part by elongated slot means, one part of each arm having a plurality of tapped bores therein spaced apart lengthwise of the respective slot, and a plurality of sets of screw means are threaded into the associated bores for securing selected adjusted positions of the movable arm parts.

7. The brace of claim 6, further characterized in that each plurality of bores comprises three bores and each set of screw means comprises a pair of screws, the screws being selectively usable in any pair of bores in the associate arm part so as to vary the range of adjustability.

8. The brace of claim 1, further characterized in that the back pad is provided at each lateral side portion with a slot, each right and left securing means is a strap affixed to the associated side pad passed through the associated back pad slot and returned to the respective side pad, each latter pad having thereon an outwardly projecting stud, and each strap having therein a plurality of apertures spaced lengthwise of the strap for selective connection to the associated stud so that the straps are adjustable to conform to different body dimension.

9. The brace in claim 8, further characterized in that each strap is provided at its free end with a finger loop to facilitate tensioning of the strap.

10. The brace defined in claim 1, further characterized in that the movable arm parts are metallic, the respective pads are of plastic material and are bonded to the associated movable arm parts.

*11. A hyperextension brace including*

*a main cruciform structure adapted to overlie the anterior thoracic area of the human body having*

*a rigid vertical arm secured to a rigid horizontal arm,*

*upper and lower arms selectively movable and securable throughout a given range to upper and lower ends of said vertical arm,*

*right and left arms selectively movable and securable throughout a given range to the right and left ends of said horizontal arm,*

*a sternum pad attached to the free end of said upper movable arm,*

*a pubic pad attached to the free end of said lower movable arm,*

*a right side pad attached to the free end of said right movable arm,*

*a left side pad attached to the free end of said left movable arm,*

*said right and left side pads adapted to be positioned at the front of the sides of the body,*

*a back pad for contact with the back of the body,*

*right and left means for attaching the back pad to the right and left side pads,*

*a plurality of means for securing the movable parts in individually selected positions whereby said brace can be adjusted to fit all standard adult sizes.*

*12. The device of claim 11, wherein at least the sternum pad is flexible about a plurality of axes with respect to said upper movable arm so as to render it capable of more readily conforming to the sternum area with which it is associated.*

*13. The device of claim 11, wherein the sternum pad is of a generally arcuate shape as seen from the front, having a concave upper edge portion, a convex lower edge portion, and side edge portions joining the aforesaid portions.*

*14. The device of claim 13, wherein the pubic pad is of a shape and size identical to the sternum pad permitting a single die to punch both pads during the manufacture thereof.*

*15. The device of claim 11 wherein each movable arm is carried on its respective fixed arm by elongated slot means, one part of each arm having a plurality of tapped bores therein spaced apart lengthwise of the respective slot, and a plurality of screw means are threaded into the associated bores for securing selected adjusted portions of said movable arms.*

*16. A hyperextension brace including*

*a main cruciform structure adapted to overlie the anterior thoracic area of the human body having*

*a rigid vertical arm secured to a rigid horizontal arm,*

*movable upper and lower arms selectively secured to upper and lower ends of said vertical arm,*

*movable right and left arms selectively secured to right and left ends of said horizontal arm, whereby said rigid and movable arms are arranged such that the structure is limited to a thickness of two arms.*

*17. A hyperextension brace including a rigid main cruciform structure adapted to overlie the anterior thoracic area of the human body and having upper and lower vertically aligned vertical arms and right and left horizontally aligned horizontal arms, sternum and pubic pads disposed respectively at the free ends of the upper and lower arms and right and left side pads disposed respectively at the free ends of the right and left arms, a back pad for contact with the back of the body and right and left means for attaching the back pad to the right and left pads, characterized in that each arm is of two-piece construction comprising a fixed part forming a rigid part of the cruciform structure and a movable part longitudinally adjustable relative to its fixed part, the pads being affixed respectively to the movable parts, and a slot, bore and screw means are provided for securing the movable parts in individually selected positions.*

*18. The device of claim 4 wherein the pubic pad is of a shape and size identical to the sternum pad permitting a single die to punch both pads during the manufacture thereof.*

* * * * *